United States Patent [19]
Hakky et al.

[11] Patent Number: 5,564,436
[45] Date of Patent: Oct. 15, 1996

[54] AUTOMATIC ROTATING CASSETTE MULTIPLE BIOPSY DEVICE

[76] Inventors: Said I. Hakky, 8547 Merrimoor Blvd. E., Largo, Fla. 34647-3145; Perry B. Hudson, 2225 Park St. North, St. Petersburg, Fla. 33710

[21] Appl. No.: 531,716

[22] Filed: Sep. 21, 1995

[51] Int. Cl.$^6$ .................................................. A61B 10/00
[52] U.S. Cl. ........................................ 128/754; 606/186
[58] Field of Search .................................. 606/167, 170, 606/184, 180, 186; 128/751, 752, 753, 754, 749

[56] References Cited

U.S. PATENT DOCUMENTS

| | | | |
|---|---|---|---|
| 5,234,000 | 8/1993 | Hakky et al. | 128/754 |
| 5,415,182 | 5/1996 | Chin et al. | 606/170 |

*Primary Examiner*—Max Hindenburg
*Assistant Examiner*—Pamela L. Wingood
*Attorney, Agent, or Firm*—John Lezdey

[57] ABSTRACT

An automatic biopsy devices for taking plural samples of tissue of a patient. The device is pneumatically operated in response to an actuator activated by the operator and makes use of a removable cassette in which a plurality of stylets are located. The stylets are disposed on a moveable tray within the cassette and are arranged to be selectively positioned within the device for propulsion through a releasably mounted cannula at a high speed into the tissue to be sampled. Each stylet includes a groove adjacent its distal end into which the tissue to be sampled enters when the cannula is propelled into the tissue. Thereafter and in automatic response to the propulsion of the stylet through the cannula into the tissue, the cannula is propelled over the stylet to excise the tissue within the stylet's recess. The propulsion of the stylets and cannula is so rapid that the tissue sampling procedure is virtually pain-free. An indicator is provided so that the operator will know the number of samples taken. The cassette is removable from the device and can be filled with the fixative solution or taken to a laboratory for analysis of the tissue samples, all the while protecting the tissue samples and the personnel handling them.

9 Claims, 9 Drawing Sheets

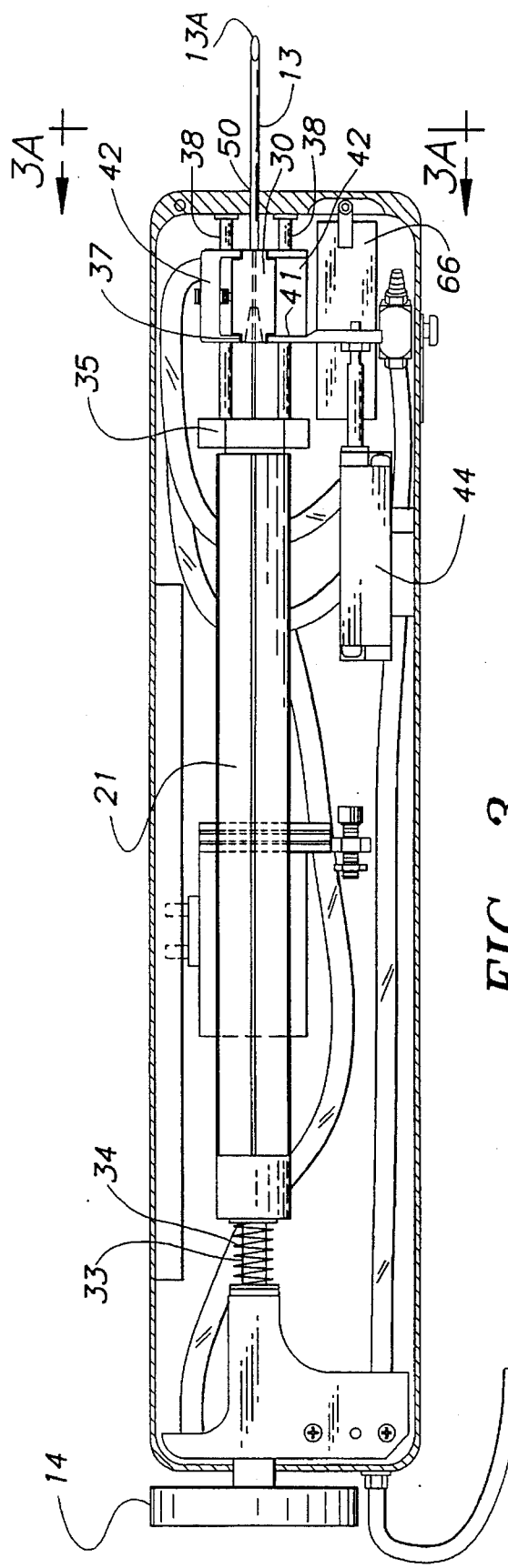
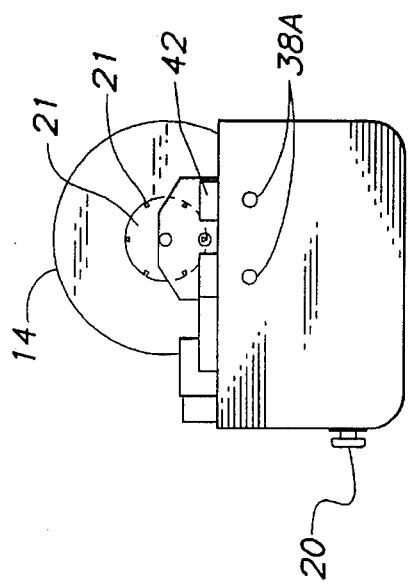
FIG. 3
FIG. 3A

AUTOMATIC ROTATING CASSETTE MULTIPLE BIOPSY DEVICE

FIELD OF THE INVENTION

The present invention relates to biopsy devices and more particular to a powered automatic biopsy device which is capable of taking a rapid succession of biopsy samples. The invention also relates a novel cassette which can be used with the device.

BACKGROUND OF THE INVENTION

In the study of tissue, a biopsy, which is a sample of tissue extracted from the body, is taken. It is desirable that at least six tissue samples are taken in order to ensure accuracy of the study. It is also desirable to obtain a succession of tissue samples as quickly and painlessly as possible.

It is further desirable that handling of the tissue samples be conducted to protect both the samples and the of handling personnel.

U.S. Pat. No. 5,234,000 to Hakky et al discloses a powered biopsy device having a plurality of stylets which are disposed in a removable cassette that is placed in the housing. After all the samples are taken the cassette is removed and the samples are taken to a laboratory where they are removed for analysis. The device does not contain any means to detect which needles have been fired.

Finally, with other prior art devices, the stylets and samples are handled on an individual basis. The tissue samples are often damaged or destroyed due to improper handling. There is also possibility of loss or mislabelling of the samples.

A need thus exists for a powered biopsy device which can take a plurality of tissue samples painlessly in rapid sequence, and wherein stylets bearing the tissue samples taken are automatically placed into a case which can be removed from the device for study in such a way that the handling personnel and the samples are protected.

OBJECTS OF THE INVENTION

Accordingly, it is the general object of this invention to provide a biopsy device which overcomes the shortcomings of the prior art.

It is a further object of this invention to provide an automatic biopsy device which applies power to the stylet and cannula for rapid insertion and removal from the tissue being sampled.

It is still a further object of this invention to provide an automatic biopsy device which is capable of taking a plurality of tissue samples in rapid succession.

It is yet a further object of this invention to provide an automatic biopsy device which controls the penetration of the stylet and cannula into the organ being sampled.

It is yet a further object of the instant invention to provide an automatic biopsy device which does not require the manual penetration of the organ whose tissue is being sampled.

It is yet a further object of the instant invention to provide an automatic biopsy device which does not require the manual handling of each individual stylet after the sample has been taken.

It is yet a further object of the invention to provide an automatic biopsy device which permits protected and safe handling of the stylets and biopsy samples after the samples have been taken thereby.

SUMMARY OF THE INVENTION

These and other objects of this invention are achieved by providing a device for taking a plurality of samples of tissue from a patient. The device comprises a housing having a portion arranged to be held by a person using the device, a reciprocating cannula having a proximal portion and a distal portion and being coupled to the housing. A plurality of stylets are located in removable rotatable cassette in the housing, with each of the stylets having a proximal end, a distal end, and a recess located adjacent to the distal end. The cassette is associated with an external indicator which shows the number of stylets used.

An actuating system, e.g., a pair of pneumatic cylinders, associated valves, and an operating means, are provided for selectively propelling each of the stylets through the cannula and into the body of the patient, e.g., in response to the depression of a trigger, so that a portion of the tissue enters into the recess of the selected stylet. The actuating system propels, e.g., in automatic response, the cannula over the selected stylet to cause the distal portion of the cannula to excise the portion of tissue within the recess of the selected stylet.

The actuating system is also arranged, to move the selected stylet and the cannula out, of tissue in the body of the patient.

In accordance with one preferred aspect of this invention each stylet is propelled into the tissue being sampled at a high rate of speed and the cannula is propelled over the stylets at a high rate of speed. These actions tend to minimize, if not eliminate, pain to the patient.

In accordance with another preferred aspect of the invention the stylets are located within a rotatable cassette which is removable from the device. The stylets with the tissue samples therein are referenced by the device into the cassette for removal as a unit therefrom for testing so that the samples and personnel handling them are protected. An affixing solution can be added to the cassette.

DESCRIPTION OF THE DRAWINGS

Other objects and many of the attendant advantages of this invention will be readily appreciated when the same becomes better understood by reference to the following detailed description, when considered in connection with the accompanying drawing, wherein:

FIG. 3 is a side view of the cassette with the cover off;

FIG. 3A is a front view of the device of FIG. 2;

DETAILED DESCRIPTION OF THE PREFERRED EMBODIMENTS

Figure 1:
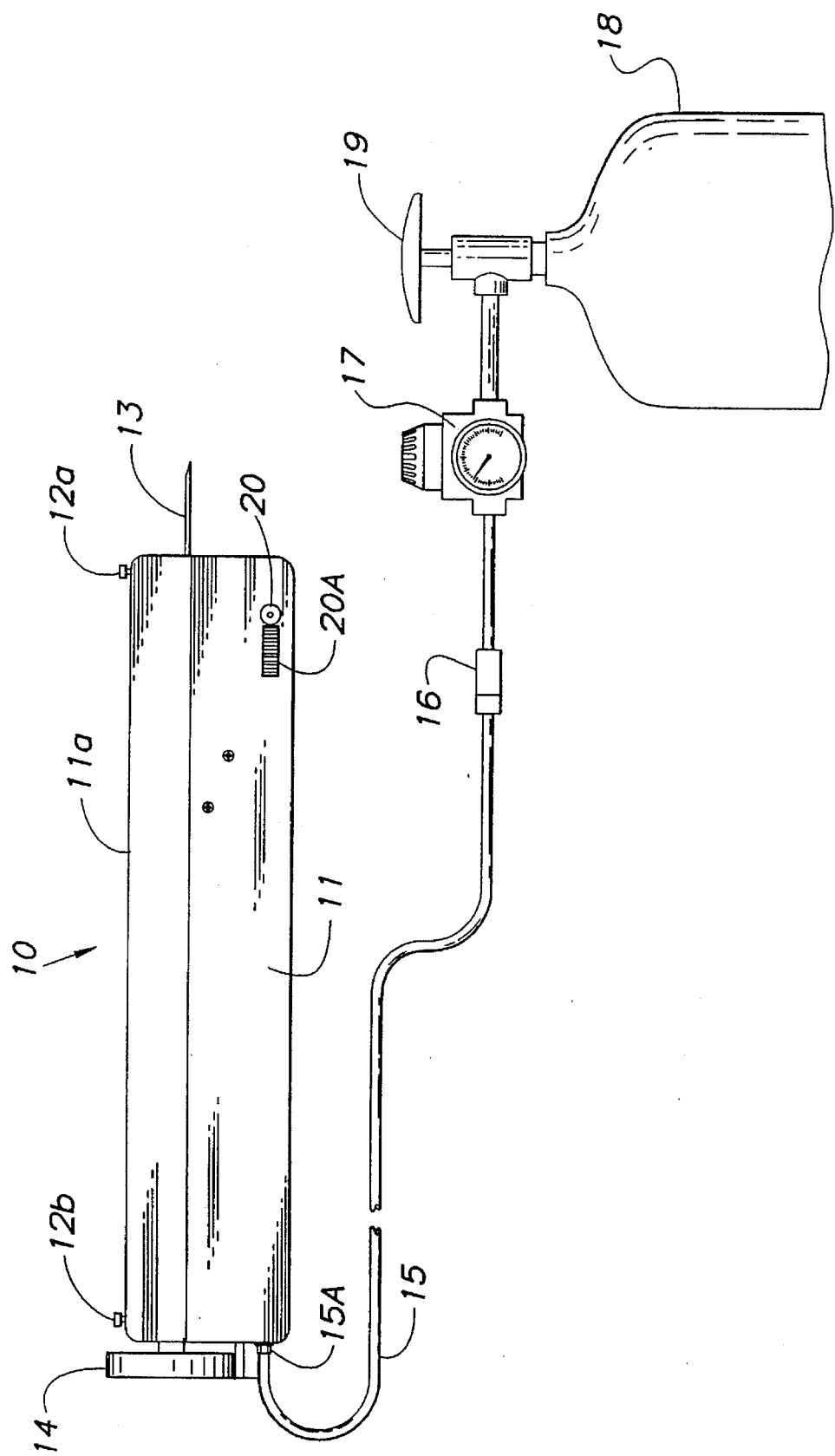
FIG. 1 is a side elevational view of the automatic biopsy device of the present invention.

Referring now to the various figures of the drawing wherein like reference characters refer to like parts, and more particularly in FIG. 1, there is shown an automatic biopsy instrument or device 10 consisting of housing 11 having a removable cover plate 11a which is held on the housing 11 by screws 12a, 12b. At one end of the housing 11 is a cannula 13 and at the other end is an indicator 14. The device 10 is connected through line 15 to a source of compressed gas 18 through a connection 16. The gas pressure is regulated by a valve 19 with a gauge 17. The device 10 is placed into operation with a actuator 20 which is associated with a safety 20A which prevents inadvertent activation of the device.

Figures 2, 2A:
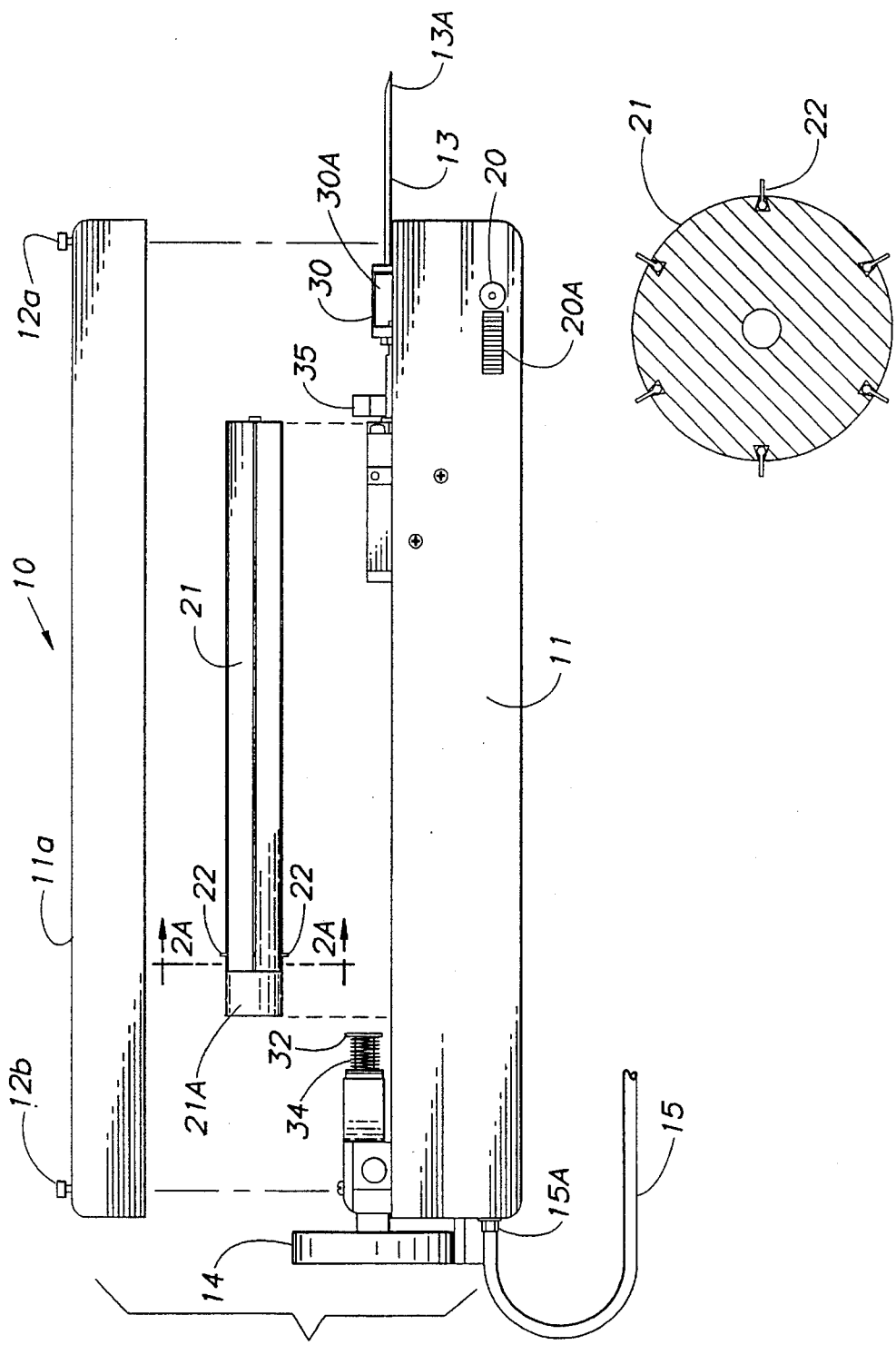
FIG. 2 is an side elevational view of the device of FIG. 1 with the cover removed showing the cassette.
FIG. 2A is a view of the cassette of FIG. 2 along line I—I is a top view of the device of FIG. 2.
Figure 4:
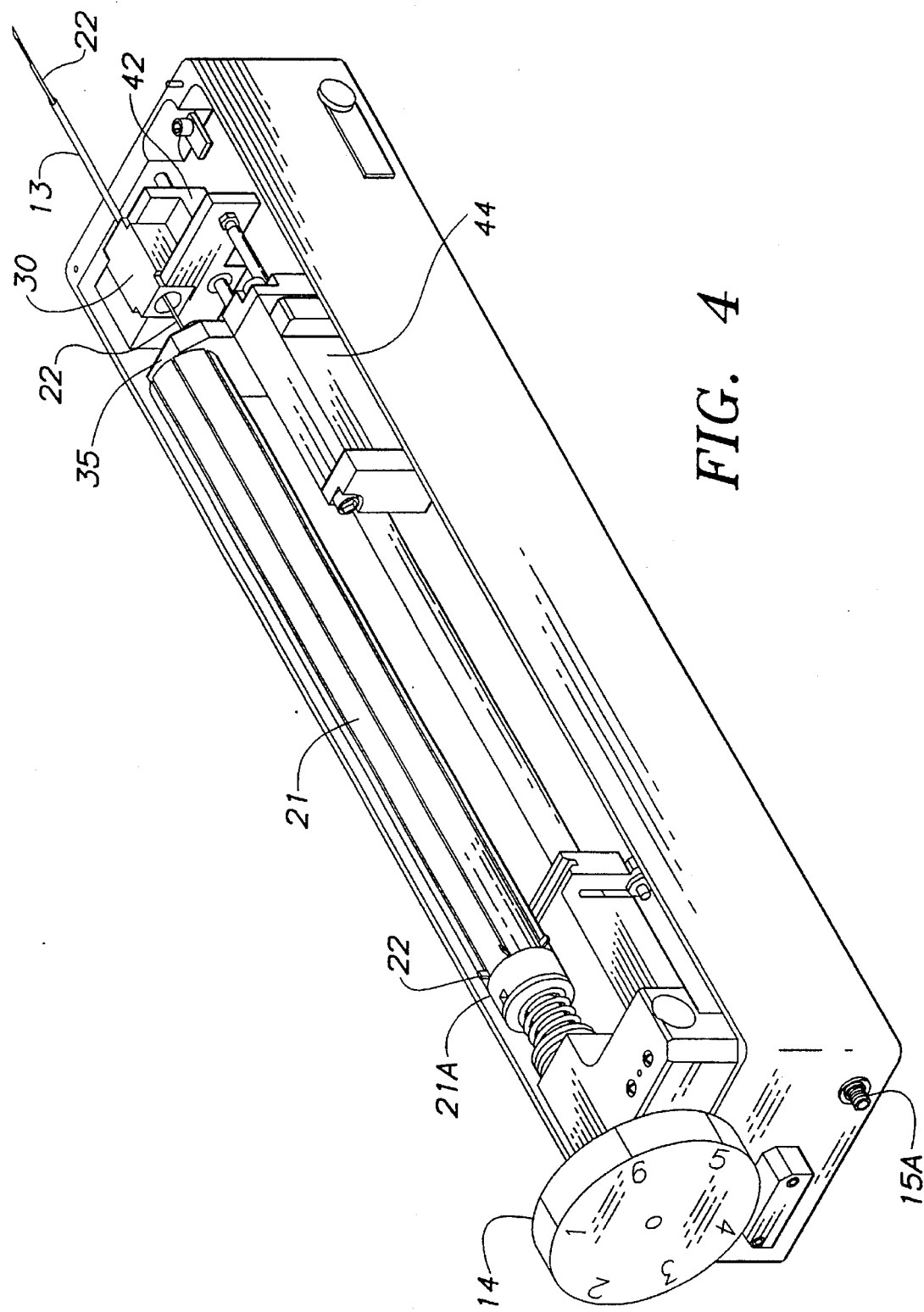
FIG. 4 is perspective view of the device of FIG. 2.

FIGS. 2 and 3 shows the device 10 with the cover 11a removed so as to insert or remove a cassette 21 containing a plurality of stylets 22 into the device 10. The cassette 21 at end 21A has a detent into which the face 32 of a rod 33 is placed. The rod 33 is normally extended forward by means of a spring 34 so that the cassette 21 is pressed against block 35. Block 35 contains an aperture to allow passage of the stylets into the cannula 13.

Figure 6:
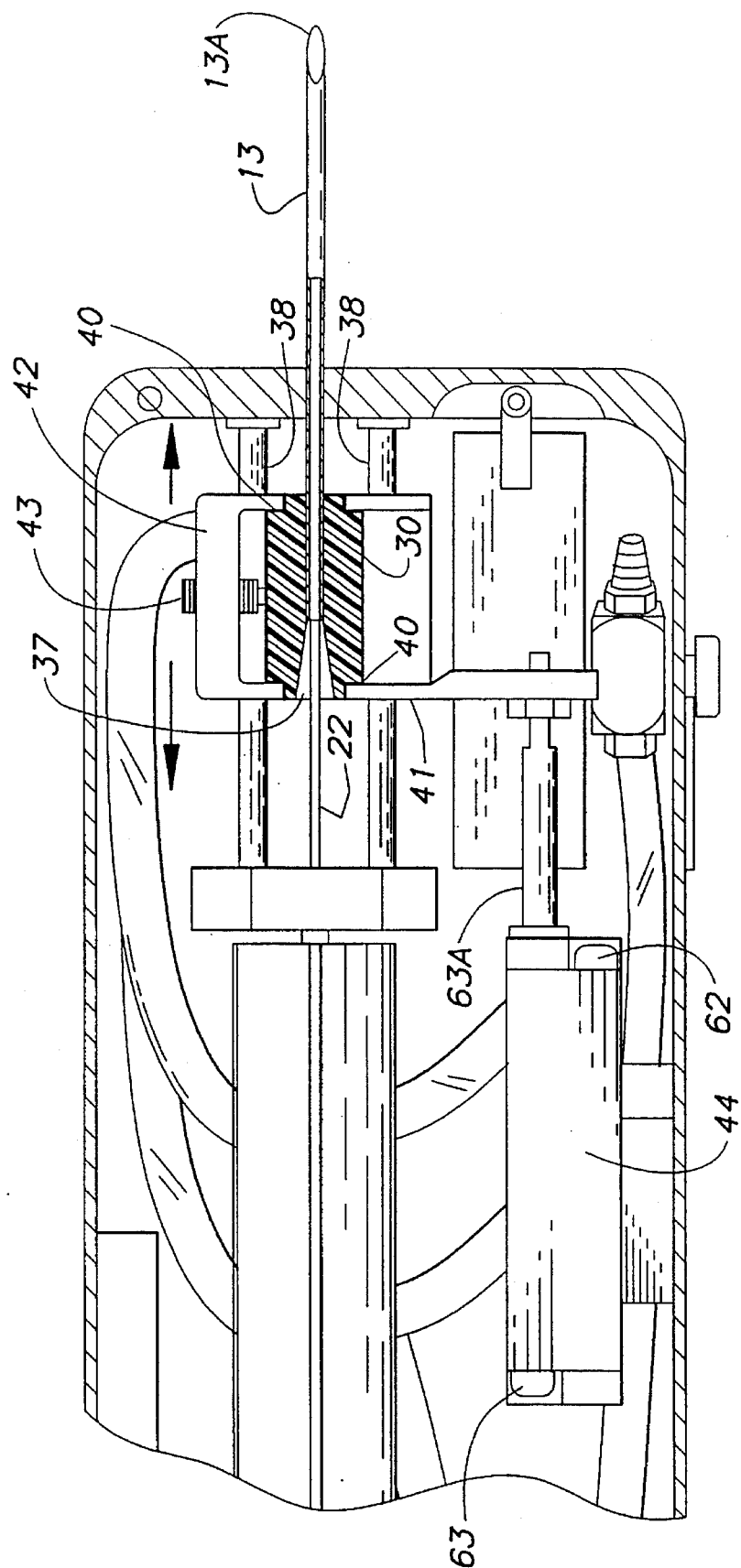
FIG. 6 is a sectional view of the distal end of the device of FIG. 5.

As seen in FIG. 6, the cannula assembly basically comprises an elongated tubular member 13 having a free distal end 13A cut at an angle to the longitudinal axis of the cannula to form a sharp cutting edge. The proximal end of the cannula assembly is in the form of the heretofore mentioned mounting block 30. The block 30 is formed of any suitable material, e.g., plastic, and includes a flared inlet toward 37 at its proximal face and which communicates with the hollow interior of the tubular cannula 13. Each corner of the block 30 includes a recess 40 therein which is arranged to receive respective edges of upstanding walls 41 of the cannula carrier 42 to hold the cannula in place on the carrier. A set screw 43 is provided in one of the walls of the carrier 42 to engage the block 30 to lock the cannula assembly on the carrier 42.

The carrier 42 is mounted on a pair of rod-like guide rails 38 to enable the carrier to be slid along the rails, i.e., reciprocated, by the movement of the piston of cylinder 44. The guide rails are mounted within the housing via associated screws 38A (FIG. 3A). The cannula 13 extends out of the housing of via a slot 50 in the front end thereof when the cannula assembly is mounted on the carrier.

The action of the piston to cause reciprocation of the carrier 42 is similar to that described in U.S. Pat. No. 5,234,000, which is herein incorporated by reference.

Figures 5A, 5B, 5C:
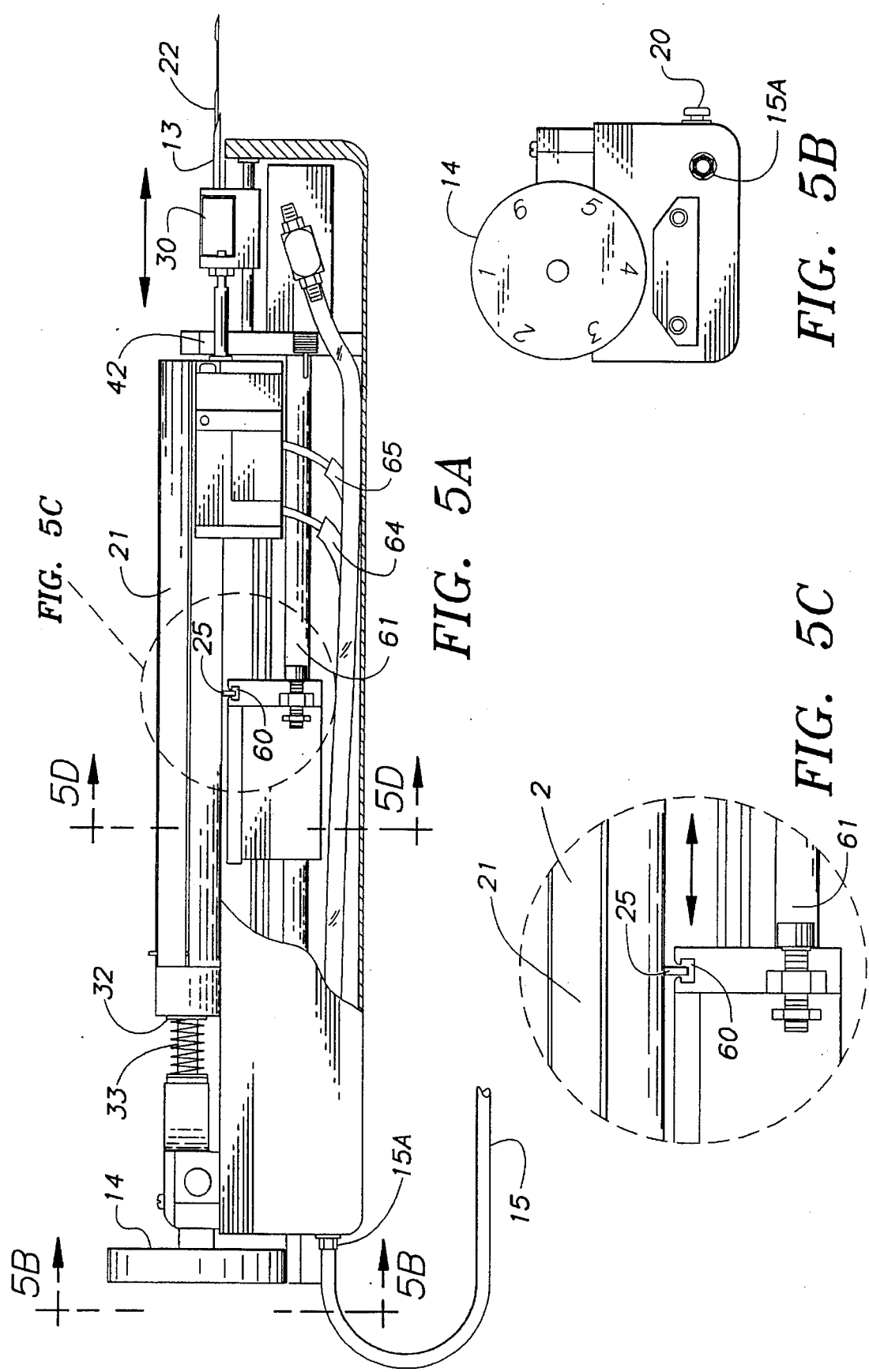
FIG. 5A is a sectional view of the distal end of the device.
FIG. 5B is rear view of the device.
FIG. 5C is an enlarged sectional view of the actuating system shown in FIG. 5A.
Figure 5D:
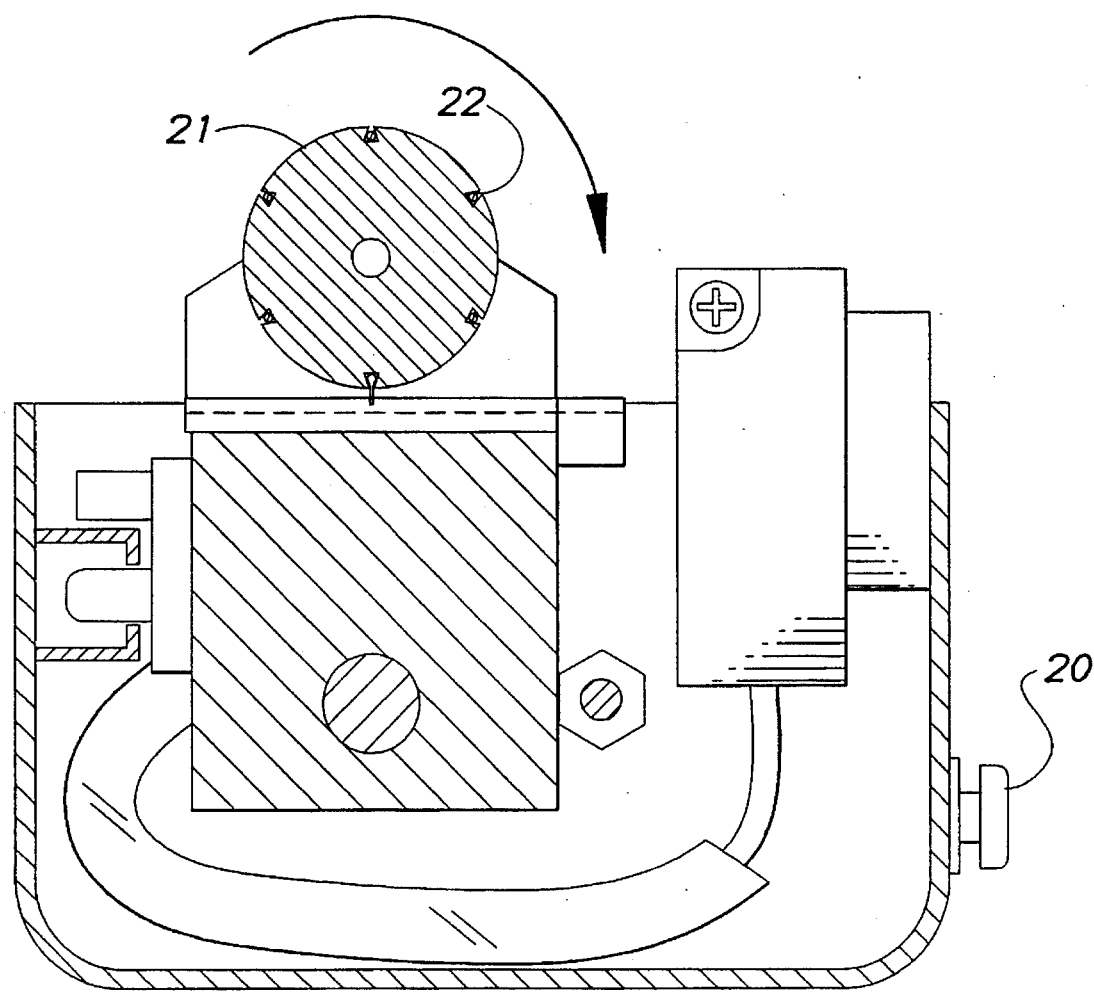
FIG. 5D is a sectional view taken along line II—II of FIG. 5A.

The extension and retraction of the stylets and the cannula 13 are accomplished utilizing a pneumatic drive system disclosed in U.S. Pat. No. 5,234,000. The system basically comprises a pair of pneumatic cylinders 62, 63 driven by a compressed gas. The first cylinder 62 includes a piston 61 which has a catch 60 which engages the proximal end 25 of a stylet to effect the extension and retraction of the engaged stylet (FIG. 5A and 5C). The second cylinder 63 includes a piston 63A which is connected to the carrier 42. The carrier 42 supports the cannula assembly and particularly its mounting block 30 to effect the extension and retraction of the cannula with respect to the housing.

The movement of the piston 61 of the cylinder 62 in the distal direction to cause the extension of a selected stylet out of the cassette 21 and through the cannula 13 to penetrate or pierce the tissue to be sampled is effected by providing the compressed gas into the proximal end of the pneumatic cylinder housing 62 via an input line 64. The movement of the piston the proximal direction to cause the retraction of the stylet back through the cannula 13 and into the cassette 21 is effected by providing the compressed gas into the distal end of the pneumatic cylinder 62 via another input line 65.

In order to control which of the input lines 64 or 65 provides the compressed gas to the cylinder 62, a reversing valve 66 and associated components are provided within the housing. The operation of the reversing valve 66 is controlled by a manually actuatable button 20. The button 20 is coupled to the reversing valve and is arranged so that when it is depressed the valve allows compressed gas to enter into input line 64. This action immediately causes the piston 61 and the stylet coupled thereto to move in the distal direction to extend the distal end of the stylet and its associated recess out of the free end of the cannula and into the tissue of the patient. The reversing valve comprises the system disclosed in U.S. Pat. No. 5,234,000.

Figure 7:
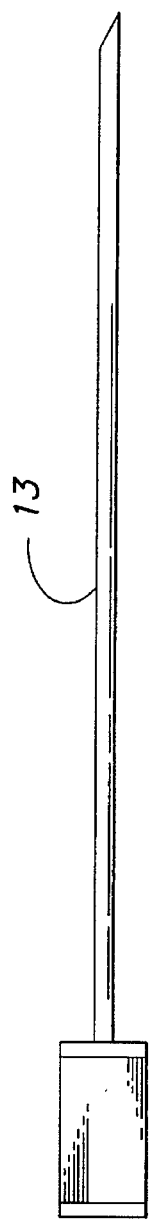
FIG. 7 is a side view of the cannula of the invention.
Figure 8:
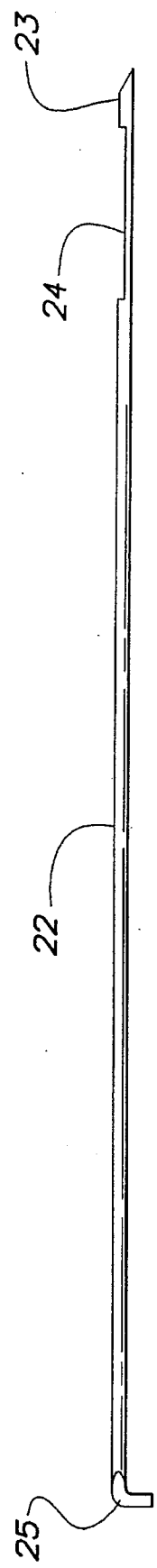
FIG. 8 is a side view of the stylet of the invention.
Figure 9:
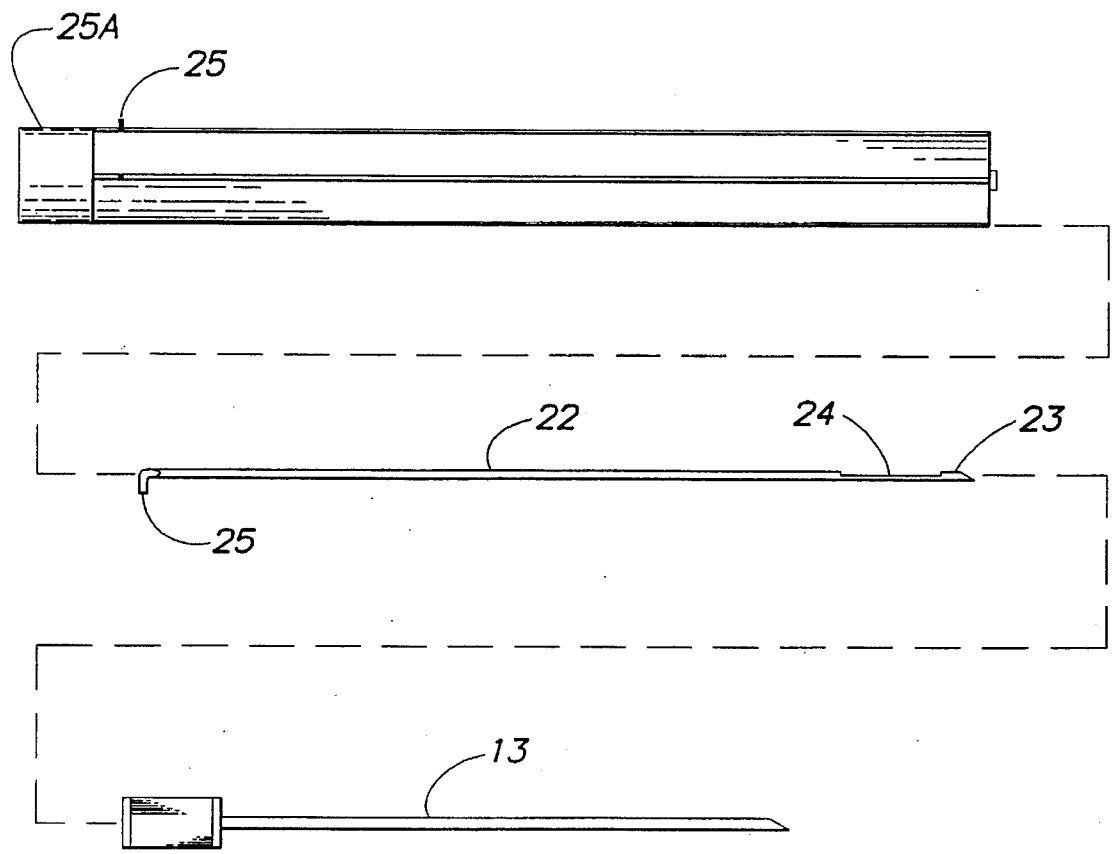
FIG. 9 shows the cooperation of the cassette, cannula and stylet of the invention.

As shown in FIGS. 7–9, each stylet 22 includes a pointed distal end 23 having an elongated notch or recess 24 adjacent thereto and a protrusion 25 at its proximal end. The recess 24 is arranged to receive a portion of tissue to be excised so that when the cannula 13 is slid thereover the tissue within the recess is cut or sliced away from the remaining tissue to the patient and held within the recess.

A plurality of the stylets 22 are placed into recesses in the cassette 21 so that the protrusions 25 extend out of the cassette 25 to reciprocate the stylet 22 within the cannula 13. The stylets are arranged in recesses in the cassette 21 so that when the cassette 21 rotates each time a stylet is aligned with the cannula 13 and the indicator means rotates together with the cassette to note the stylet to be used. Thereafter, the device is operated to cause the stylet to be propelled into and out of the cannula 13 so that a portion of tissue is excised, i.e., sheared off by the passing cannula. The device then operates to retract both the stylet back with the desired tissue taken into the cassette and the cannula from the tissue being sampled. In its simplest form the indicator can be used to rotate the cassette.

In accordance with the preferred embodiment on the invention, the device 10 may be used to sequentially take tissue samples by the use of respective stylets and to place the samples into the cassette. Since only the cannula 13 and stylets make contact with the patient, and since these are replaceable, the device with a new cassette of stylets and a new cannula can be used immediately on another patient or be sterilized.

The overall operation of the automatic biopsy device 10 to take plural tissue samples will now be discussed, To that end, a cassette having fresh stylets therein is inserted into the housing between the mounting means.

The surgeon then manipulates the device 10 so that the free end of the cannula 13 inserted in the patient's body is located at a position adjacent the tissue to be sampled. It should be pointed out at this juncture that when the device 10 is to be introduced through a lumen or other opening in the patient's body, e.g., transurethrally, transrectally, a shield 10, (not shown) is placed over the cannula 13 to protect the patient from its sharp end.

The aiming of the tip of the cannula to the desired position and orientation is preferably effected by use of ultrasound or any other form of imaging.

Some present medical procedures call for multiple, e.g., six, biopsy samples of a patient. The device 10 of this invention enables the surgeon to take such samples without having to withdraw the device from the patient's body or to reload it with stylets. In this regard, with the device disclosed herein the surgeon can quickly and easily take up to six tissue samples by merely aiming the instrument, releasing the safety and pressing the actuator for each sample to be taken. Moreover, the stylets are quite long, e.g., 170 mm, and are arranged to extend out of the cannula 13 by a substantial distance, so that the tip of the cannula 13 need not be manually inserted in the organ to be tested, as has characterized the prior art. Instead, the pneumatic cylinder will provide such action at high speed thereby reducing pain or trauma.

For the taking of biopsies through the surface of the body, e.g., to biopsy organs such as the liver or kidney, the local area of the body surface is first anesthetized and the skin and underlying tissue is pierced by manually pressing the cannula 13 so that its piercing tip enters into the patient's body to a location adjacent the tissue/organ to be sampled. The device may then be operated as described earlier, i.e., pressing the actuator 20 in sequence to cause the stylets to take tissue samples in sequence. This operation can be accomplished virtually as fast as the trigger can be depressed, released, re-depressed, re-released, and so on.

After all the biopsies have been taken, the cassette may be removed from the device 10. The cassette, can then be transported to the laboratory safely and without the danger of injury to personnel or to the tissue samples. Moreover, the cassette can be immersed in a fixative fluid which prevent the samples from drying out prior to testing. If additional tissue samples are needed of the patient a new cassette can be inserted in the device while the device remains in place with the cannula extending into the patient's body.

The cassette and the stylets held therein, and the cannula assembly are preferably in the form of a replaceable, disposable kit arranged for use with the automatic biopsy device 10 described heretofore. Thus, no manual handling of the stylets is required, and they can be maintained in sterile condition.

As stated previously, the embodiment shown herein uses a pneumatic system, operated by compressed air or carbon dioxide, to drive the stylets and cannula forward and then in reverse. However, the invention will work just as well with other gases or with other types of powered drives, such as hydraulic or electric. Furthermore, although the embodiment disclosed herein shows a cassette tray with six stylets for the taking of six biopsies, cassettes with more or less stylets can be provided. Moreover, the length of the stylets may be selected to control the depth of penetration provided thereby. Thus, for some applications shorter stylets may be used and for other applications longer stylets may be used.

As should be appreciated from the foregoing, an automatic biopsy device of this invention enables a surgeon, using one hand, to take a plurality of biopsies in rapid sequence by successively depressing a trigger. The device may be powered by electric, pneumatic, hydraulic or other means. At the conclusion of the taking of the biopsies, the cassette with the stylets having tissue samples therein can be removed by merely pressuring the rod 33. The cassette can then be taken to the laboratory after fixative solution like 10% Formalin or Bouin solution for study and analysis, with the cassette's body protecting the samples and the personnel handling the samples.

Moreover, the device 20 of this invention does not require the manual piercing of the tissue to take the specimen and assures that the biopsy is taken at the proper location, because the length of the stylets determine the penetration into the body and into the organ to be sampled. This is particularly advantageous because existing devices do not protect against under-insertion of the stylet, which results in a sampling of the wrong tissues, or over-insertion of the stylets which can cause damage to the organ.

Without further elaboration the foregoing will so fully illustrate our invention that others may by applying current or future knowledge, readily adapt the same for use under the various conditions of service.

What is claimed is:

1. A device for taking a plurality of tissue samples which comprises:

a housing, a cannula coupled at one end of said housing and reciprocating therein;

a rotatable and removable cassette mounted for rotation within said housing, said cassette housing a plurality to stylets which are arranged so as to be aligned with said cannula on rotation;

means for selectively propelling a stylet into said cannula so as to enter tissue to be sampled, and then retracting said stylet into said cassette;

actuating means for propelling said cannula over said stylets with tissue;

means for rotating said cassette; and indicator means mounted at the other end of said housing associated with said cassette for indicating the number of stylets utilized.

2. The device of claim 1 wherein each of said stylets is brought back into said housing by said actuating means after it has been moved out of said tissue.

3. The device of claim 2 wherein each of said stylets is brought back into said cassette by said actuating means after it has been moved out of said tissue.

4. The device of claim 1 wherein said cassette comprises a plurality of grooves and each of said plurality of stylets is positioned in a respective one of said grooves.

5. The device of claim 1 wherein said actuating means propels said stylets and said cannula very quickly to minimize pain to said being.

6. The device of claim 1 wherein said actuating means additionally comprises first reversing valve means coupled to a first pneumatic cylinder and second reversing valve means coupled to a second pneumatic cylinder.

7. The device of claim 1 wherein said propulsion of said cannula over said selected stylet occurs in automatic response to the propulsion of said stylet to a predetermined position within said cannula.

8. The device of claim 7 wherein said propulsion of said cannula over said selected stylet occurs in automatic response to the propulsion of said stylet to a predetermined position within said cannula.

9. The device of claim 1 wherein said cannula is releasably secured to said device.

* * * * *